United States Patent [19]
Chen et al.

[11] Patent Number: 5,954,719
[45] Date of Patent: Sep. 21, 1999

[54] SYSTEM FOR OPERATING A RF ABLATION GENERATOR

[75] Inventors: Peter Cheng Chen, Irvine; Tho Hoang Nguyen, Huntington Beach, both of Calif.

[73] Assignee: Irvine Biomedical, Inc., Irvine, Calif.

[21] Appl. No.: 09/046,237

[22] Filed: Mar. 23, 1998

Related U.S. Application Data

[63] Continuation-in-part of application No. 08/763,614, Dec. 11, 1996, Pat. No. 5,782,828.
[51] Int. Cl.$^6$ .................................................. A61B 17/36
[52] U.S. Cl. ............................... 606/42; 606/34; 607/102
[58] Field of Search .................................. 606/32–34, 41, 606/42; 607/100–105, 115, 116, 122

[56] References Cited

U.S. PATENT DOCUMENTS

| | | |
|---|---|---|
| 4,095,602 | 6/1978 | Leveen . |
| 4,114,622 | 9/1978 | Gonser . |
| 4,934,377 | 6/1990 | Bova et al. . |
| 5,334,193 | 8/1994 | Nardella ..................................... 606/41 |
| 5,383,917 | 1/1995 | Desai et al. .............................. 607/102 |
| 5,540,722 | 7/1996 | Clare et al. . |
| 5,573,533 | 11/1996 | Strul ......................................... 606/34 |
| 5,581,470 | 12/1996 | Pawloski . |
| 5,582,609 | 12/1996 | Swanson et al. .......................... 606/39 |
| 5,583,467 | 12/1996 | Loewenguth et al. . |
| 5,628,771 | 5/1997 | Mizukawa et al. ...................... 607/102 |
| 5,637,947 | 6/1997 | Kising et al. . |
| 5,643,197 | 7/1997 | Brucker et al. ........................... 604/20 |
| 5,769,847 | 6/1998 | Panescu et al. ........................... 606/42 |

*Primary Examiner*—Michael Peffley

[57] ABSTRACT

A catheter-based system for operating a RF ablation generator comprising a RF splitter for delivering RF energy to a plurality of electrodes; a low-pass filter located between the RF splitter and an external EKG monitor for displaying real-time signal to said EKG monitor; and a software program having temperature data input from a plurality of temperature sensors and signal output capability, wherein the software program sends out signals to the RF splitter being adapted to control the RF energy output to each electrode.

14 Claims, 5 Drawing Sheets

*SYSTEM INSTALLATION DIAGRAM*

SYSTEM FOR OPERATING A RF ABLATION GENERATOR

RELATIONSHIP TO COPENDING APPLICATION

This application is a continuation-in-part of application Ser. No. 08/763,614, filed on Dec. 11, 1996, now U.S. Pat. No. 5,782,828, the entire contents of which are incorporated herein by reference.

FIELD OF THE INVENTION

The present invention generally relates to a medical device system and its use for endocardiac mapping and ablation. More particularly, this invention relates to a catheter-based system and its methods, by operating a RF ablation generator with an ablation apparatus, in conjunction with temperature control mechanisms, in the treatment of atrial flutter and atrial fibrillation indications.

BACKGROUND OF THE INVENTION

Symptoms of abnormal heart rhythms are generally referred to as cardiac arrhythmias, while an abnormally rapid rhythm is referred to as a tachycardia. The presence of an arrhythmogenic region or an accessory pathway in the atria can bypass or short circuit the normal pathway, potentially resulting in very rapid heart contractions, referred to here as atrial flutter. Atrial flutter is generally characterized by a saw tooth pattern with negative deflections in inferior leads of the ECG, while the atrial rate is in the range of 240–340 beats per minute. Atrial fibrillation is a more complicated case of multiple atrial flutters, resulting in a chaotic and non-regular arrhythmia.

Treatment of atrial flutter and atrial fibrillation (AFib) may be accomplished by a variety of approaches, including drugs, surgery, implantable pacemakers/defibrillators, and catheter ablation. While drugs may be the choice of treatment for many patients, they only mask the symptoms and do not cure the underlying causes, and they may also cause side effects. Implantable devices only correct the arrhythmia after it occurs. Surgical and catheter-based treatments, on the other hand, will actually cure the problem, usually by ablating the abnormal arrhythmogenic tissues or the accessory pathways responsible for the tachycardia.

Atria Fibrillation is believed to be the result of an aberrant conduction of electrical signals within the atria, resulting in a condition in which the transmission of electrical activity becomes so disorganized that the atria contracts quiveringly. Once considered a benign disorder, AFib is now widely recognized as the cause of significant morbidity and mortality. The most dangerous outcome from AFib is thromboembolism and stroke risk, the latter due to the chaotic contractions of the atria, causing blood to pool. This in turn can lead to clot formation and the potential for an embolic stroke. According to data from the American Heart Association, approximately 75,000 strokes per year are AFib-related.

While radiofrequency catheter ablation, using current catheter design, has produced promising results, the known catheter usually has only one large electrode for ablation purposes. In the AFib patient, because of the simultaneous occurrence of multiple wavelets of re-entry electrical impulses within the atria, it is necessary to stop the multiple re-entry impulses simultaneously or sequentially through the creation of an endocardial linear lesion. A catheter with multiple flexible curves on the distal portion to accommodate the anatomic structure of the atrium surface has been disclosed in the patent application Ser. No. 08/763,614 now U.S. Pat. No. 5,782,828. It is the purpose of this invention to provide an improved catheter-based ablation system with the appropriate software program in the treatment of atrial flutter and atrial fibrillation indications.

SUMMARY OF THE INVENTION

In general, it is an object of the present invention to provide a catheter-based system that is used for ablation of atrial flutter and atrial fibrillation. It is another object of this invention to provide a catheter-based system comprising a software program or algorithm to supply about equal amount of RF energy density to each of the electrodes. The "RF energy density" in this patent is defined as the RF energy delivered per unit of tissue-contact surface area. It is still another object of the present invention to provide a catheter-based system for a contiguous linear lesion, having about the same lesion characteristics for each individual lesion portion of the overall contiguous linear lesion. The "lesion characteristics" in this invention is defined as including the lesion width, the lesion length, the lesion depth, and/or severity of the lesion. In general, the lesion characteristics are similar when two lesions are created by about the same amount of RF energy density (energy/area) under the conditions of good electrode-to-tissue contact.

A catheter-based system of this invention for ablating the aberrant electrical conduction pattern of the atrial flutter and atrial fibrillation comprises: a catheter having a tubular elongate having a distal section, a distal end, a proximal end, and at least one lumen extending therebetween, wherein a plurality of electrodes is disposed of on the distal section; wherein a handle means is attached to the proximal end of the tubular elongate, and wherein a conducting wire is secured to each electrode; a RF generator having an electrical energy input and RF energy output capabilities, a controlling mechanism means, and a RF splitter, wherein the RF energy output is supplied to each electrode through each individual conducting wire; a plurality of the temperature sensing means, wherein the temperature sensing means is located at the proximity of each electrode, and wherein the temperature is constantly sensed and relayed to the controlling mechanism means; and a software program connected to the controlling mechanism means, the software program having the temperature data input and signal output capabilities, wherein the software program sends out signals to the RF splitter adapted to control the RF energy output to each of the electrodes at a predetermined temperature range, and wherein the sum of the total duration of the RF energy output within the predetermined temperature range, delivered to each electrode, is individually predetermined.

These objects, as well as others, are further provided in a method of operating a catheter-based RF generator system comprising the steps of: inserting a catheter into the heart chamber and positioning the catheter at the targeted ablative site, wherein the catheter has a distal section, a distal end, a proximal end, and at least one lumen extending therebetween, wherein a plurality of electrodes is disposed of on the distal section, wherein a handle means is located at the proximal end of the catheter, wherein a conducting wire is secured to each electrode, wherein a plurality of the temperature sensing means is located at the proximity of each electrode, and wherein the temperature is constantly sensed and relayed to a controlling mechanism means; operating a RF generator, the RF generator having an electrical energy input and RF energy output capabilities, a controlling mechanism means, and a RF splitter, wherein the RF energy output is supplied to each electrode through each individual conducting wire; and operating a software program that is connected to the controlling mechanism means, wherein the software program has the temperature data input and signal output capability, wherein the software program sends out signals to the RF splitter adapted to control the RF energy output to each of the electrodes at a predetermined temperature range, and wherein the sum of the total duration of the RF energy output within the predetermined temperature range, delivered to each electrode, is individually predetermined.

In another embodiment, RF energy is applied to the tissue through each electrode, wherein the total RF energy density output to each electrode is about equal for each electrode.

In a further embodiment, an ablation catheter system further comprises a closed-loop control mechanism for each electrode having a temperature sensor. To better control the desired lesion characteristics, more RF energy may be applied to an electrode when the measured tissue contact temperature from that electrode is relatively low. On the other hand, RF energy may be minimized when a relatively high tissue contact temperature is detected. In still another embodiment, an ablation catheter system further comprises a programmed control mechanism for independently selecting and controlling the ablation electrodes of the catheter system through a RF splitter. In this case, it further comprises selecting and controlling the number of electrodes ablated in one of the following modes: a simultaneous mode, a sequential mode, a random mode, or a combination of them.

BRIEF DESCRIPTION OF THE DRAWINGS

Additional objects and features of the present invention will become more apparent, and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
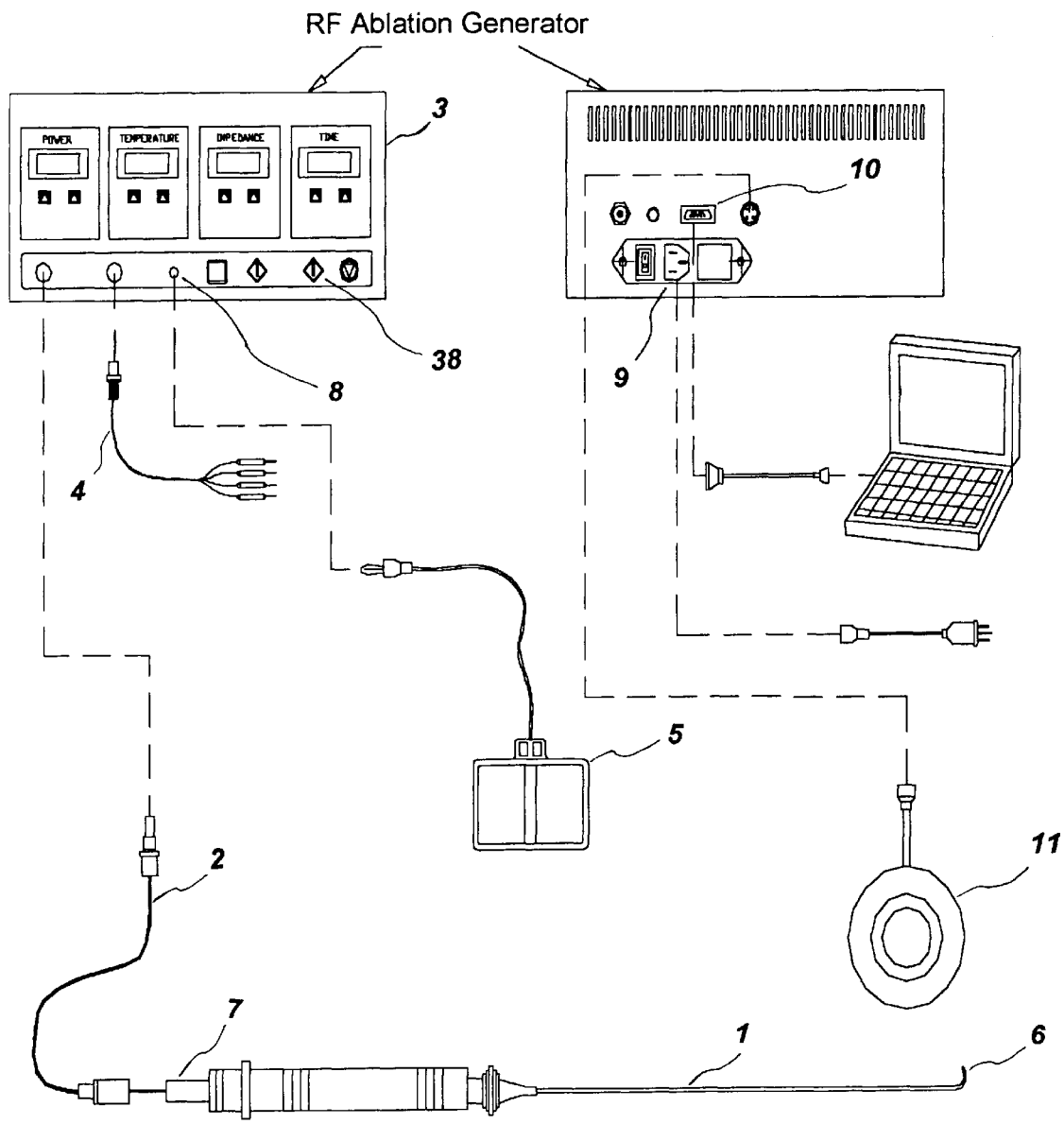
FIG. 1 is a system installation diagram constructed in accordance with the principles of the present invention.

FIG. 1 is a system installation diagram constructed in accordance with the principles of the present invention. The system comprises a catheter with multiple electrodes 1, a connecting cable 2, a RF generator 3, an EKG connecting cable 4, and a DIP electrode means 5 that is connected to the RF generator 3 through an isolated patient connector 8, wherein the DIP electrode means 5 is placed under a patient, during an ablation procedure, to provide a closed-loop circuit of the RF energy delivery system of the present invention. The catheter 1 has a plurality of electrodes 6 and a plurality of temperature sensing means, wherein each temperature sensing means is located at the proximity of each of the plurality of electrodes 6. The catheter 1 is connected to the RF generator 3 through the connecting cable 2. Each of the insulated temperature wires and the conducting wires of the catheter 1 are secured to a connector 7 contact pin of the catheter 1. Therefore, the measured temperature data from each of the multiple electrodes is relayed to a control mechanism means located in the CPU board 14 of the RF generator 3. In the meantime, the RF energy output is delivered through each of the conducting wires to an individual electrode on the catheter 1.

The EKG connecting cable 4 is used to transmit the electrical signal to an external EKG monitor (not shown) to display the EKG signal for each of the electrodes 6. At the back panel of the RF generator 3, there is a power supply port 9 and a data output port 10. An optional footswitch 11 is also provided for the user's convenience. Either the footswitch 11 or a button 38 on the front panel of the RF generator 3 can be used to start and stop the RF energy delivery.

Figure 2:
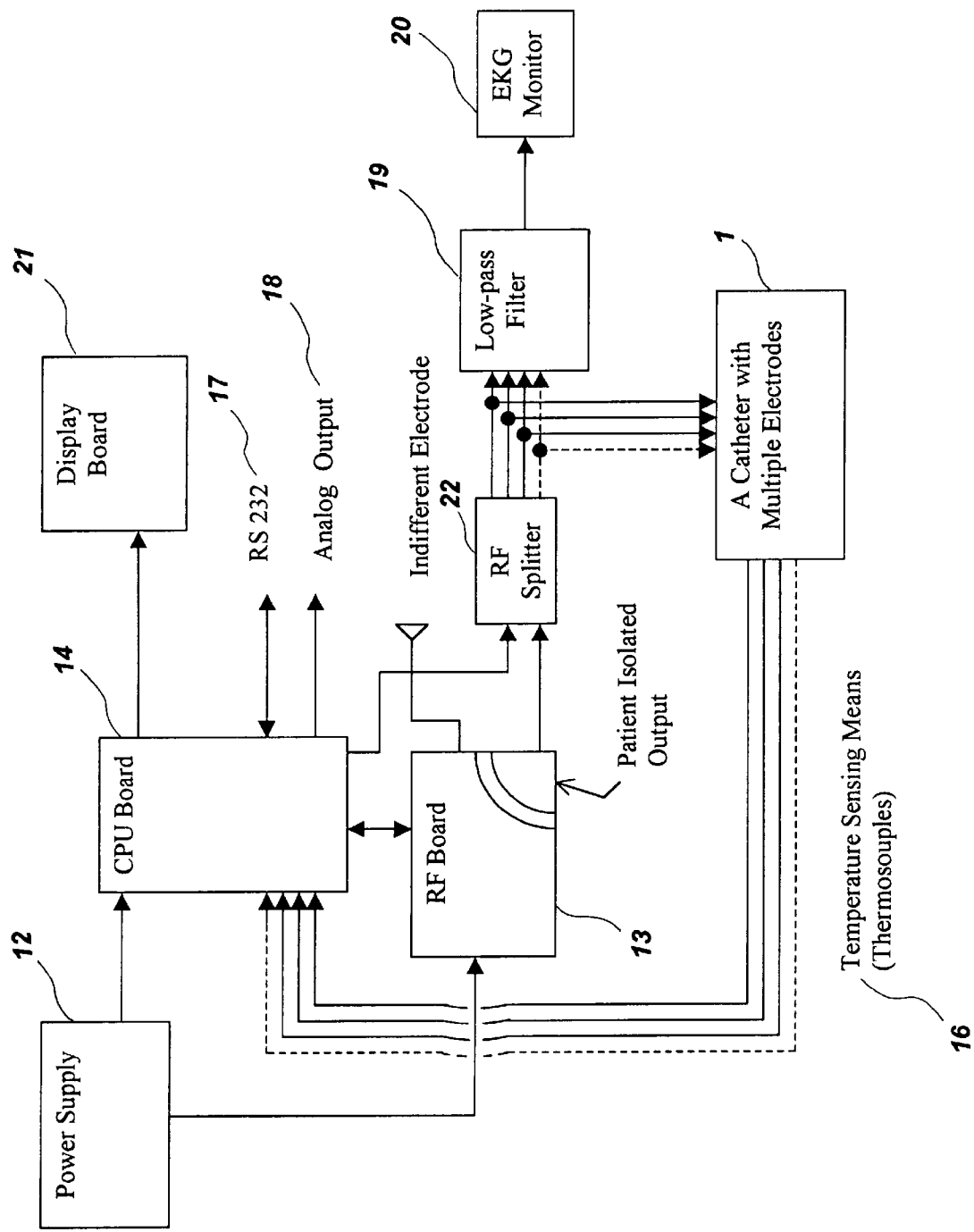
FIG. 2 is a block diagram of the catheter-based system comprising RF energy delivery through a RF splitter to each of the multiple electrodes of an ablation catheter.

FIG. 2 is a block diagram of the catheter-based system comprising RF energy delivery through a RF splitter to each of the multiple electrodes of the ablation catheter 1. The power supply source 12 is connected to the RF generator having the RF board 13 and the CPU board 14, wherein a software program becomes an integral portion of the CPU board 14. A catheter that has multiple electrodes, has a plurality of temperature sensing means 16, wherein each temperature sensing means is associated with each of the electrodes 6. The measured temperature data is relayed to the software program inside the CPU board 14. The data from the CPU board 14 is then displayed via a display board 21. The command or instruction is issued from the CPU board 14 to the RF board 13 to control the RF energy output. A RF splitter 22 is employed to split the RF energy to one or more of the conducting wires, wherefrom thereafter the RF energy output is relayed to the corresponding electrode or electrodes. A low-pass filter 19 is used to continuously feed the EKG signal to the EKG monitor 20 for real-time display. The controlling mechanism means of the catheter system only allows ablation when the real-time cardiac electrical signal assures that the catheter is still at a proper location. All data can be stored in the CPU 14 or transmitted through either RS232 17 or an analog output port 18 to an external computer for data analysis.

Figure 3:
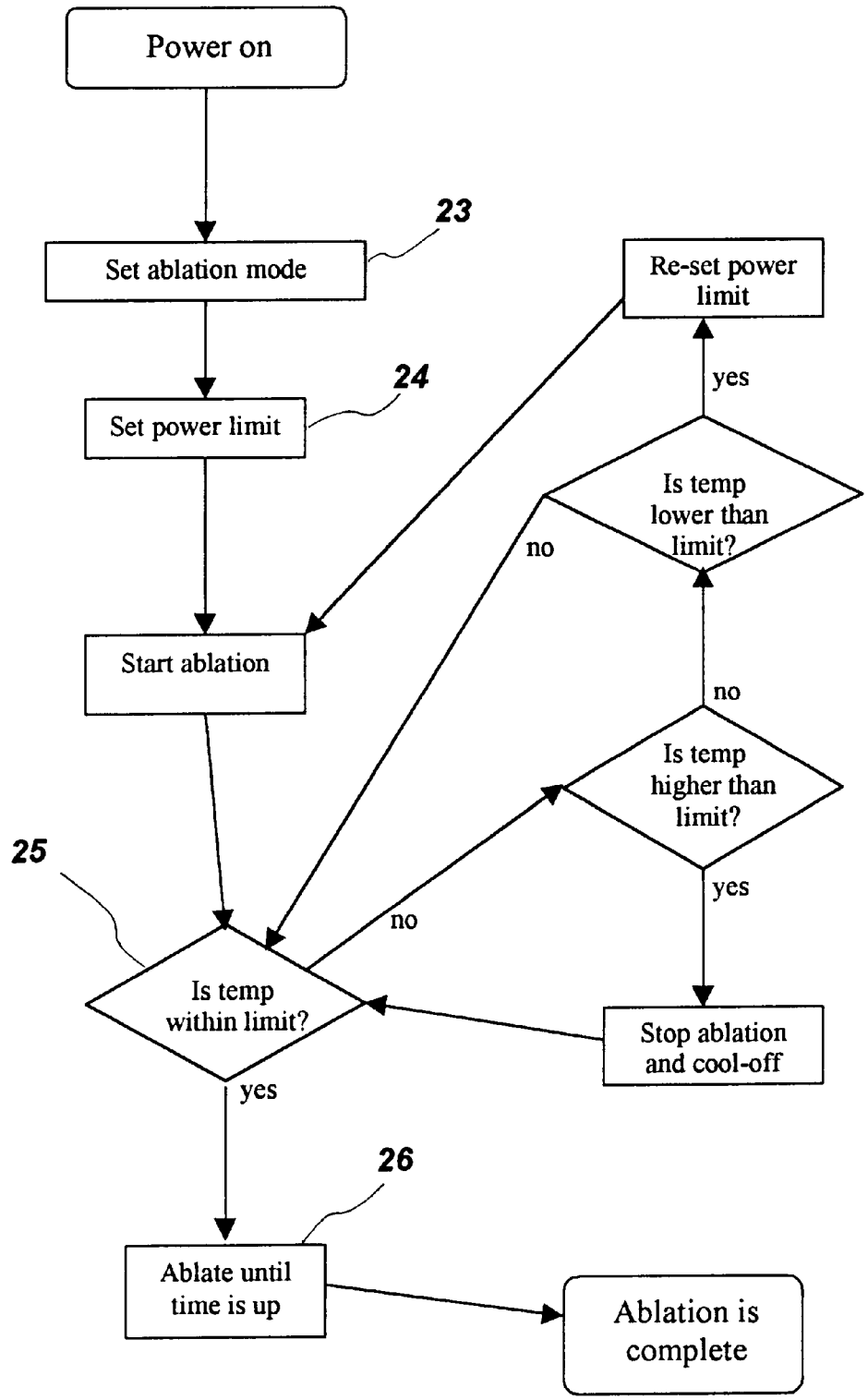
FIG. 3 is block diagram of the software program for the catheter-based generator system.

FIG. 3 is a block diagram of the software program for the catheter-based generator system. The major steps in the software program comprise: "set ablation mode" block 23, "set power limit" block 24, "is temp within limit?" block 25 and "ablate until time is up" block 26. The ablation mode 23 includes one of the modes: a simultaneous mode, a sequential mode, a random-order mode, or a combination of the above. The power limit 24 is initially set at a relatively low value for safety reasons. An example would be to set the initial power limit at 15 watts. The power limit can be raised in appropriate increments until a final power limit of the RF generator is reached. One example for the final power limit would be 150 watts. The temperature limit 25 is set for a range, which is appropriate for the ablative lesion. One example would be to set the ablation temperature limit as 67.5° C.±2.5° C. The "time is up" is a predetermined time duration for ablating any of the electrodes. One example would be to set the time limit for electrode no. 1 as 30 seconds. More details are shown in the section of Mode of Operations.

Figure 4:
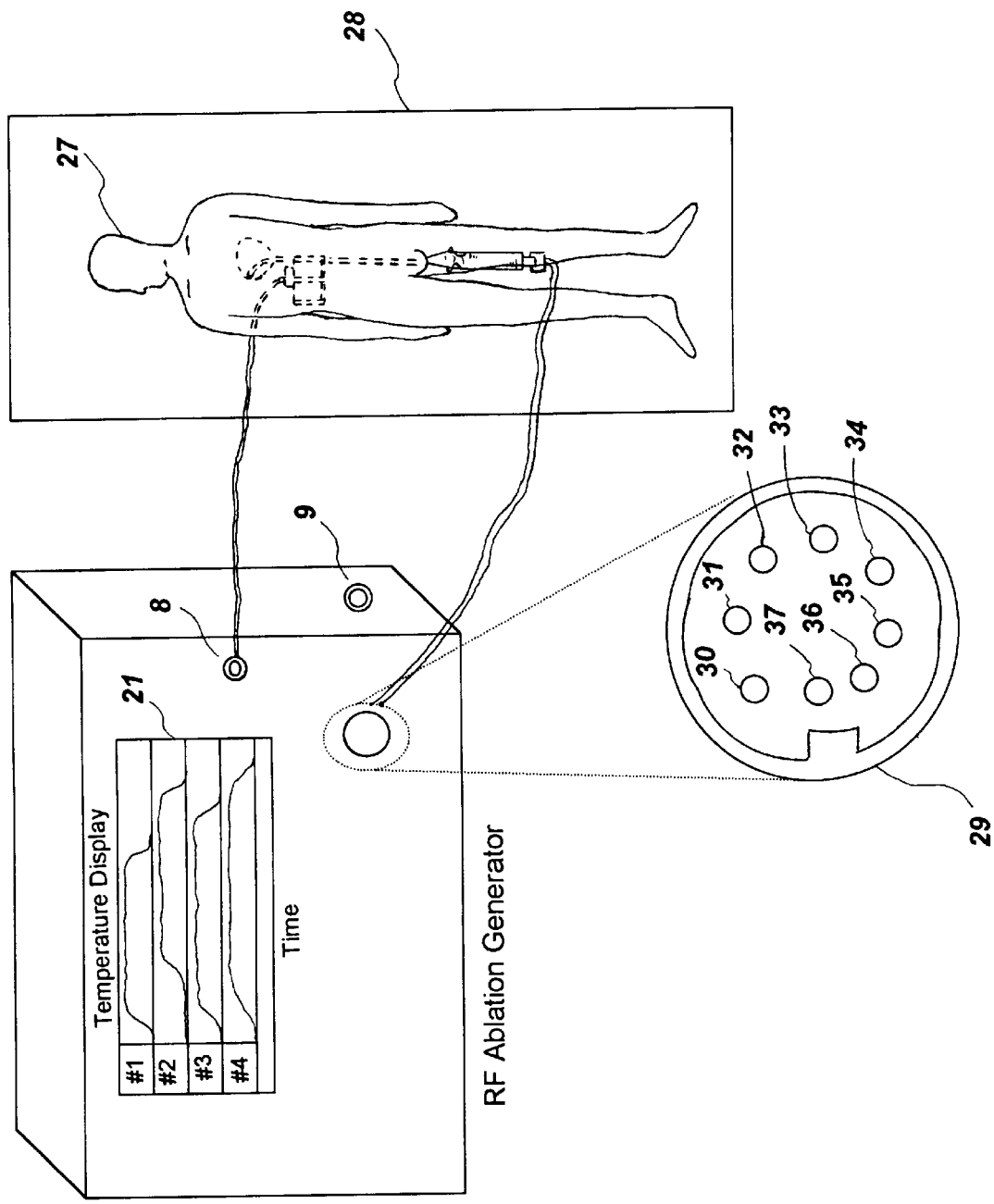
FIG. 4 is a diagram of the system using an ablation catheter having multiple electrodes and a multiple temperature sensing means in association with a RF generator means.

FIG. 4 shows a diagram of the system using an ablation catheter having multiple electrodes and multiple temperature sensing means in association with a RF generator means. During an ablation procedure, a patient 27 lies down on an operating table 28. The DIP electrode 5, which is placed under the body of the patient 27, is connected into the patient isolation output port 8. The catheter 1 is inserted into the heart chamber of the patient through a femoral vein. The proximal end of the catheter 1 is connected to a catheter connecting cable 2, wherein the connector end 29 of the connecting cable 2 is shown in FIG. 4. For illustration purposes, the connector end 29 of a quadrapolar catheter has at least eight contact pins. The contact pins 30, 31, 32, and 33 are connected to the four conducting wires, which are thereafter secured to the tip, the 2nd, the 3rd, and the 4th electrodes, respectively. The contact pins 34, 35, 36, and 37 are used for thermocouple wiring purposes. In this case, the four pairs (30 & 34), (31 & 35), (32 & 36), and (33 & 37) are adopted for the thermocouple wiring for the tip, the 2nd, the 3rd, and the 4th electrodes, respectively. The display board 21 shows the temperature data as a function of time.

In another embodiment, RF energy is applied to the tissue surrounding the predetermined number of electrodes of the catheter of this invention to effect the ablation of atrial flutter or atrial fibrillation. The electrodes are formed of conducting materials selected from the group consisting of platinum, iridium, gold, silver, stainless steel, Nitinol, or an alloy of their mixture. The electrodes are selected from the group of a coil electrode, a tubular electrode, a needle electrode, or a microporous electrode.

In an alternate embodiment, the catheter-based RF generator system of this invention further comprises a steering mechanism that is located at the handle means to cause at least one deflection for the distal section. Usually a rotating ring or a push-pull plunger is employed in the steering mechanism. In another embodiment, the steerable ablation catheter comprises a bi-directional deflection or a multiple curve deflection of the distal section. One end of the steering wire is attached at a certain point of the distal section of the said catheter body. The other end is attached to the steering mechanism at the handle. The steering mechanism on a steerable catheter or device is well-known to those who are skilled in the art.

Figure 5:
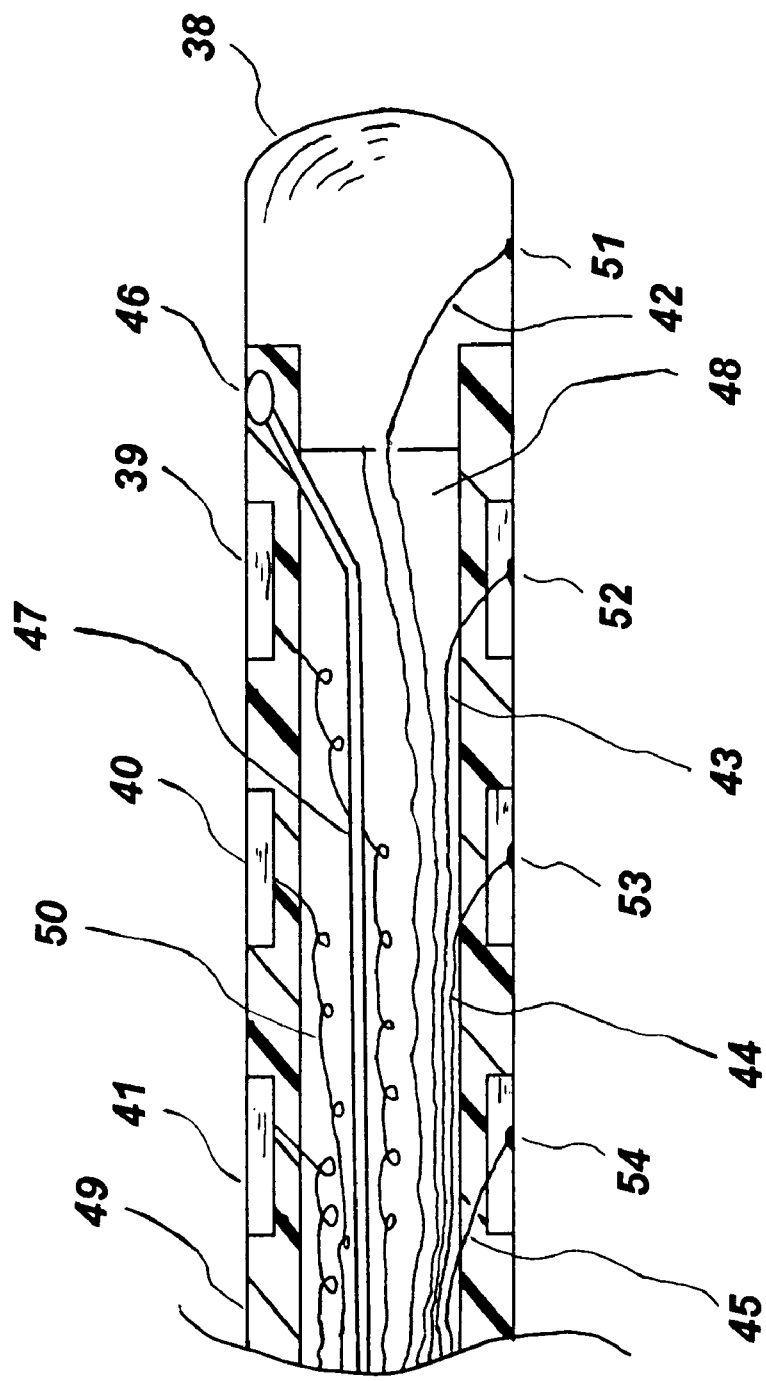
FIG. 5 is a cross-sectional view of an ablation catheter used in association with the catheter-based ablation system.

FIG. 5 shows a cross-sectional view of the distal section of an ablation catheter 1 used in association with the catheter-based ablation system of this invention. In one embodiment, the catheter comprises a tubular elongate 49 having a distal section, a distal end, a proximal end, and at least one lumen 48 extending therebetween, wherein a plurality of electrodes 38–41 is disposed of on the distal section; wherein a handle means is attached to the proximal end of the tubular elongate 49, and wherein a conducting wire 50 is secured to each of the electrodes; a plurality of the temperature sensing means 51–54, wherein the temperature sensing means is located at the proximity of each electrode, and wherein the temperature is constantly sensed and relayed to the controlling mechanism means via the insulated pair of wires 42–45 in association with its corresponding conducting wires.

The catheter further comprises an optional fluid irrigation means, wherein the fluid is introduced into the lumen 48 of the tubular elongate 49 and is adapted to diffuse out of the catheter 1 through at least one outlet port 46. The fluid is selected from the group consisting of saline, cooled saline, oxygenated saline, heparin solution, antibiotic fluid, or anti-inflammatory fluid.

Therefore at ablation time, the fluid is continuously or intermittently supplied through the conduit to evenly cover and rinse the electrodes so that the impedance rise at the contact site is substantially reduced. The fluid flow rate is preferably in the range of 2 cc/min. to 20 cc/min. By cooling off the electrode during ablative energy delivery, optimal ablation efficiency is achieved.

The invention also comprises a method and a system for controlling the flow rate of fluid through the lumen to optimize the cooling effect of the energy delivering electrodes of the catheter. The control system preferably regulates the flow rate based on signals representative of the temperature of the catheter tip and/or tissue impedance.

MODE OF OPERATIONS NO. 1

For illustration purposes, a quadrapolar electrophysiology catheter with four electrodes and four temperature sensing means is inserted into the atrium of a patient. The catheter is placed at the atrial flutter site and is ready for ablation procedure. By referring to FIG. 3, in the ablation operation with a simultaneous mode, the power limit is initially set at 60 watts. The RF energy is splitted into the four electrodes. The temperature at each tissue-electrode contact site is measured and relayed to the CPU. When the temperature is within the limit, say 67.5° C.±2.5° C., the ablation continues until the predetermined time limit, say 30 seconds, is over. When the temperature rises above the set limit, the RF power is temporarily turned-off by the software program. After a predetermined period of, say 15 seconds, the ablation re-starts again. The temperature is constantly monitored and used for control purposes. By using the simultaneous mode, the four electrodes shall be essentially the same size, and the lesion characteristics from the four electrodes shall be essentially the same. In one embodiment, the sum of the total duration of the RF energy output delivered to each electrode is essentially equal.

MODE OF OPERATIONS NO. 2

For illustration purposes, a quadrapolar electrophysiology catheter with four electrodes and four temperature sensing means is inserted into the atrium of a patient. The catheter is placed at the atrial flutter site and is ready for ablation procedure. By referring to FIG. 3, in the ablation operation with a sequential mode, the power limit is initially set at 15 watts. The RF energy is relayed to the first electrode. The temperature at its tissue-electrode contact site is measured and relayed to the CPU. When the temperature for that electrode is within the limit, say 67.5° C.±2.5° C., the ablation continues until the predetermined time limit, say 30 seconds, is over. When the temperature for that electrode exceeds the set limit, the RF power is temporarily turned-off by the software program. After a predetermined period of cooling-off, say 15 seconds, the ablation restarts again. The temperature is constantly monitored and used for control purposes. After the first electrode ablation is completed, switch the RF power to the next electrode and repeat the ablation operation until all the electrodes are done. Because each of the four electrodes can vary in size, location, and other physical properties, the use of a sequential mode of ablation is preferred, so that the lesion characteristics from each of the four electrodes can be similar.

MODE OF OPERATIONS NO. 3

For illustration purposes, a quadrapolar electrophysiology catheter with four electrodes and four temperature sensing means is inserted into the atrium of a patient. The catheter is placed at the atrial flutter site and is ready for ablation procedure. By referring to FIG. 3, in the ablation operation with a combination of simultaneous and sequential modes, the power limit is initially set at 50 watts. The RF energy is relayed to all four electrodes. The temperature at all four tissue-electrode contact sites are measured and relayed to the CPU. When all the temperatures are within the limit, say 67.5° C.±2.5° C., the ablation continues until the predetermined time limit, say 30 seconds, is over. When any of the four temperatures exceeds the set limit, the RF power is temporarily turned-off by the software program. After a predetermined period of cooling-off, say 5 seconds, the RF energy delivery to the other three electrodes re-starts again. The temperature is constantly monitored and used for control purposes. After a second electrode ablation is completed, split the RF power to the next electrodes that have not met the predetermined time duration. Repeat the ablation operation until all the electrodes have met the requirements of the temperature limit for the predetermined time period for each electrode. By using a combination of the sequential and simultaneous modes, the ablation efficiency can be optimized. The ablation efficiency in this invention is defined as the total ablation time. The shorter the ablation time, the less exposure a patient endures to the fluoroscope. Over-exposure to the fluoroscope results in a higher skin cancer risk.

From the foregoing, it should now be appreciated that an improved catheter-based system having a plurality of electrodes, a RF generator and software program for optimal mapping and/or ablation. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter-based RF generator system comprising:

a catheter having an elongate tubular element having a distal section, a distal end, a proximal end, and at least one lumen extending therebetween, wherein a plurality of electrodes is disposed on the distal section; wherein a handle means is attached to the proximal end of the elongate tubular element, and wherein a conducting wire is secured to each electrode;

a RF generator having electrical energy input and RF energy output capabilities, a controlling mechanism means, and a RF splitter, wherein the RF energy output is supplied to each electrode through each individual conducting wire;

a plurality of the temperature sensing means located at proximity of each of the electrodes, wherein temperature is constantly sensed and relayed to said controlling mechanism means;

a low-pass filter located between the RF splitter and an external EKG monitor for displaying real-time cardiac electrical signal on said EKG monitor so that said controlling mechanism means only allows ablation when the real-time cardiac electrical signal assures that the catheter is still at a proper location; and a software program connected to the controlling mechanism means, the software program having temperature data input and signal output capability, wherein the software program sends out signals to the RF splitter being adapted to control the RF energy output to each of the electrodes at a predetermined temperature range, and wherein the sum of a total duration of the RF energy output delivered to each electrode is individually predetermined.

2. The catheter-based RF generator system of claim 1, wherein a steering mechanism is located at the handle means to cause at least one deflection for the distal section, wherein the steering mechanism comprises a steering wire, one end of the steering wire being attached at a certain point of the distal section while another end of the steering wire being attached to the steering mechanism at the handle means.

3. The catheter-based RF generator system of claim 1, wherein the sum of the total duration of the RF energy output delivered to each electrode is essentially about equal.

4. The catheter-based RF generator system of claim 1, wherein the mode of the RF energy delivery to each electrode is selected from the group consisting of a simultaneous delivery mode, a sequential delivery mode, a random delivery mode, and a combination of the above.

5. The catheter-based RF generator system of claim 1, wherein the electrodes are selected from the group consisting of a coil electrode, a tubular electrode, a needle electrode, and a microporous electrode.

6. The catheter-based RF generator system as in claim 1 further comprising a fluid irrigation means, wherein a fluid is introduced into at least one lumen of the elongate tubular element and is adapted to diffuse out of the catheter at its distal section.

7. The catheter-based RF generator system of claim 6, wherein the fluid is selected from the group consisting of saline, cooled saline, oxygenated saline, heparin solution, antibiotic fluid, and anti-inflammatory fluid.

8. A method of operating a catheter-based RF generator system comprising the steps of:

inserting a catheter into a heart chamber and positioning the catheter at a targeted ablative site, wherein the catheter having an elongate tubular element having a distal section, a distal end, a proximal end, and at least one lumen extending therebetween, wherein a plurality of electrodes is disposed on the distal section; wherein a handle means is attached to the proximal end of the elongate tubular element, and wherein a conducting wire is secured to each electrode;

operating a RF generator, the RF generator having electrical energy input and RF energy output capabilities, a controlling mechanism means, and a RF splitter, wherein the RF energy output is supplied to each electrode through each individual conducting wire; a low-pass filter located between the RF splitter and an external EKG monitor for displaying real-time cardiac electrical signal on said EKG monitor so that said controlling mechanism means only allows ablation when the real-time cardiac electrical signal assures the catheter is still at a proper location; and operating a software program that is connected to the controlling mechanism means, wherein the software program has the temperature data input and signal output capability, wherein the software program sends out signals adapted to control the RF energy output to each of the electrodes at a predetermined temperature range, and wherein the sum of the total duration of the output RF energy delivered to each electrode is individually predetermined.

9. The method of operating the catheter-based RF generator system of claim 8, wherein a steering mechanism is located at the handle means to cause at least one deflection for the distal section.

10. The method of operating the catheter-based RF generator system of claim 8, wherein the sum of a total duration of the output RF energy delivered to each electrode is essentially equal.

11. The method of operating the catheter-based RF generator system of claim 8, wherein the mode of the RF energy output delivered to each electrode is selected from the group consisting of a simultaneous delivery, a sequential delivery, a random delivery and a combination of them.

12. The method of operating the catheter-based RF generator system of claim 8, wherein at least one electrode is selected from the group consisting of a coil electrode, a tubular electrode, a needle electrode, and a microporous electrode.

13. The method of operating the catheter-based RF generator system as in claim 8, further comprising a fluid irrigation means, wherein a fluid is introduced into the at least one lumen of the elongate tubular element and is adapted to diffuse out of the catheter at its distal section.

14. The method of operating the catheter-based RF generator system of claim 13, wherein the fluid is selected from the group consisting of saline, cooled saline, oxygenated saline, heparin solution, antibiotic fluid, or anti-inflammatory fluid.

* * * * *